United States Patent
He et al.

(10) Patent No.: US 6,512,163 B1
(45) Date of Patent: Jan. 28, 2003

(54) RANK1, AN ANKYRIN-REPEAT CONTAINING PEPTIDE FROM RICE ASSOCIATED WITH DISEASE RESISTANCE

(75) Inventors: Chaozu He, Beijing (CN); Guo-Liang Wang, Dublin, OH (US)

(73) Assignee: Institute of Molecular Agrobiology (SG)

(*) Notice: Subject to any disclaimer, the term of this patent is extended or adjusted under 35 U.S.C. 154(b) by 0 days.

(21) Appl. No.: 09/525,223

(22) Filed: Mar. 14, 2000

Related U.S. Application Data

(63) Continuation-in-part of application No. PCT/SG97/00042, filed on Sep. 15, 1997.

(51) Int. Cl.$^7$ .................. C12N 15/29; C12N 15/82; C12N 15/87; C12N 5/10; A01H 5/00
(52) U.S. Cl. .................. 800/278; 435/320.1; 435/419; 536/23.6; 800/298; 800/320; 800/320.1; 800/320.2; 800/320.3
(58) Field of Search .................. 536/23.6; 435/468, 435/320.1, 419; 800/278, 279, 301, 320, 320.1, 320.2, 320.3, 298

(56) References Cited

U.S. PATENT DOCUMENTS 5,866,787 A * 2/1999 Silverman et al.

FOREIGN PATENT DOCUMENTS

| EP | 0693554 | 1/1996 |
|---|---|---|
| WO | 9416077 | 7/1994 |
| WO | 9636697 | 11/1996 |
| WO | 9749822 | 12/1997 |
| WO | 9826082 | 6/1998 |
| WO | 9851801 | 11/1998 |

OTHER PUBLICATIONS

Ronald G. Duggleby, Identification of an Acetolactate Synthase Small Subunit Gene in two Eukaryotes, 1997, Gene, pp. 245–249.*
Linthorst et al, Constitutive Expression of Pathogenesis–Related Proteins PR–1, GRP, and PR–S in Tobacco Has No Effect on Virus Infection, Mar. 1999, The Plant Cell, vol. 1, pp. 285–291.*
Cao et al 1997, The Arabidopsis NPR1 gene that controls systemic acquired resistance encodes a novel protein containing ankyrin repeats. Cell 88:57–63.*
Linthorst et al 1989, Constitutive Expression of Pathogenesis–related proteins PR–1, GRP and PR–S in tobacco has no effect on virus infection. The Plant Cell 1:285–291.*
Duggleby 1997, Identification of an acetolactate synthase small subunit gene in two eukaryotes. Gene 190:245–249.*
Baeuerie, P.A., et al., "NF–κB: Ten Years After", Cell, vol. 87, Oct. 4, 1996, pp 13–20.
Baldwin, Jr., A.S., "The NFκkB and IκB Proteins: New Discoveries and Insights", Annu. Rev. Immunol. 1996, vol. 14, pp. 649–683.
Michaely, P., et al. "The Membrane–binding Domain of Ankyrin Contains Four Independently Folded Subdomains . . . " vol. 268, No. 30, Oct. 25, 1993, pp. 22703–22709.
Görlach, J., et al., "Benzothiadiazole, a Novel Class of Inducers of Systemic Acquired Resistance, Activates Gene Expression and . . . ", The Plant Cell, vol. 8, Apr. 1996, pp. 629–643.
LaMarco, K., et al., "Identification of Ets– and Notch–Related Subunits in GA Binding Protein", Science, 1991, vol. 253, pp. 789–792.
Whiteside, S.T., et al., "I kappa B epsilon, a novel member of the IκB family, controls RelA and cRel NF–κB activity", The EMBO Journal, vol. 16, No. 6, 1997, pp. 1413–1426.
Cao et al., "The Arabidopsis NPR1 Gene That Controls Systemic Acquired Resistance Encodes a Novel Protein Containing Ankyrin Repeats", Cell, Jan. 10, 1997, vol. 88, pp. 57–63.
Ryals et al., "The Arabidopsis NIM1 Protein Shows Homology to the Mammalian Transcription . . . " The Plant Cell, Mar. 1997, vol. 9, pp. 425–439.
Cao, H., et al., "Characterization of an Arabidopsis Mutant That is Nonresponsive to inducers of Systemic Acquired Resistance", The Plant Cell, vol. 6, Nov. 1994, pp. 1583–1592.
Wang, Guo–Liang, et al., "RFLP Mapping of Genes Conferring Complete and Partial Resistance to Blast in a Durably Resistant Rice Cultivar", Genetics, Apr. 1994, vol. 136, pp 1421–1434.
Delaney, T.P., et al., "Arabidopsis signal transduction mutant defective in chemically and biologically induced disease resistance", Proc. Nat. Acad. Sci. U.S.A., Jul. 1995, vol. 92, pp. 6602–6606.

* cited by examiner

Primary Examiner—David T. Fox
Assistant Examiner—David H Kruse
(74) Attorney, Agent, or Firm—Rothwell, Figg, Ernst & Manbeck

(57) ABSTRACT

An isolated nucleic acid comprising a sequence of SEQ ID NO:2. The nucleic acid sequence can be transformed into plant cells. The nucleic acid codes for disease resistance in plants. The transformed plant cells can then be introduced to plants for regeneration of disease resistant plants.

15 Claims, 8 Drawing Sheets

```
ANK1
Rank1                      TDPAALIKYWNDP
IκB-ε     DGDTLVHLAVIHEAPAVLLCCLALLPQEVLDIQ
IκB-α     DGDSFLHLAIIHEEKALTMEVIRQVKGDLAFLN
Cactus    DGDTPLHLACISGSVDVVAALIRMAPHPCLLNI
NPR1      AAVKLELKEIAKDYEVGFDSVVTVLAYVYSSRV ANK2
Rank1     ETFRKISQAMGPLGGPDFAEPSGTEGTEEEGEY
IκB-ε     LYQTALHLAVHLDQPGAVRALVLKGASRALQDR
IκB-α     LQQTPLHLAVITNQPEIAEALLGAGCDPELRDF
Cactus    VAQTPLHLAALTAQPNIMRILLLAGAEPTVRDR
NPR1      IPELITLYQRHLLDVVDKVVIEDTLVILKLANI ANK3
Rank1     EDESIVHHTASVGDDEGLKKALDGGADKDEEDL
IκB-ε     HGDTALHVACQRQSWPVPAACWKGGPEPGRGTS
IκB-α     RGNTPLHLACFQGCLASVGVLTQSCTTPHLHSI
Cactus    HGNTALHLSCIAGEKQCVRALTEKFGATEIHEA
NPR1      IVKSNVDMVSLEKSLPEELVKEIIDRRKELGLE ANK4
Rank1     EGRRALHFVCGYGELKCAQVLLEAGAAVDALDK
IκB-ε     QGLACLHIATLQKNQPLMELLLRNGADIDVQEG
IκB-α     NGHTCLHLASIHGYLGIVELLVSLGADVNAQEP
Cactus    DGERCVHLAAEAGHIDILRLLVSHGADINAREG
NPR1      DACALHFAVAYCNVKTATDLLKLDLADVNHRNP ANK5
Rank1     NKNTPLHYAAGYGMKGCVDLLLKNGAAVTLENM
IκB-ε     SGKTALHLAVETQERGLVQFLLQAGAQVDARML
IκB-α     NGRTALHLAVDLQNPDLVSLLLKCGADVNRVTY
Cactus    SGRTPLHIAIEGCNEDLANFLLDECEKLNLETA
NPR1      RGYTVLHVAAMRKEPQLILSLLEKGASASEATL ANK6
Rank1     DGKTPIDVAKLNNQDEVLKLLEKDAFL
IκB-ε     NGCTPLHLAAGRGLMGISSTLCKAGADSLLRNV
IκB-α
Cactus    AGLTAYQFACIMNKSRMQNILEKRGAETVTPPD
NPR1
```

Alignment of RANK1's predicted amino acids sequence with IκB-ε, IκB-α, Cactus and NPR1 proteins containing ankyrin repeats.

FIG. 1

Accumulation of NPR1 RNA in blast resistant plants post-inoculation. RANK1 specific primers were used to amplify cDNAs isolated from the resistant (C101A51) and susceptible plants (C039).

| | | |
|---|---|---|
| SEQ ID 2 | Genomic | TTTACTTTGTTGAAGCTAAAACTTTGTTAGTTTTTCTGGGGCAGTTCATT |
| SEQ ID 1 | cDNA | |
| | Genomic | GATGATAATCCAGACCTCACAGGTCAACCAACAGTCCTCGGTTTCAAAAA |
| | cDNA | |
| | Genomic | AAAAAAAAAATCCCACAGTAACCTGTCCCGTTGAACATTGCACAAACTTG |
| | cDNA | |
| | Genomic | TCAGATCTGGTGCACCTCTCGTCTAGCTATAATAGTATCGAACTATGAGT |
| | cDNA | |
| | Genomic | TTCCATAACCCCGCTGTTTGTATAATTGCAGTTGGTGTGCAATGCTAGAG |
| | cDNA | |
| | Genomic | CACAAAAGTTAATGAACGACAAACTACCTTTTGATTCATTCTCTTGTGGA |
| | cDNA | |
| | Genomic | TCTAGAATGTGGTGTGAGACTTTTTTTTGGGAGCTGCATCTGCTCCTTG |
| | cDNA | |
| | Genomic | TTCACTGACTAATCAGGATTTGGGTTAAACTTTTGTTTTTCAGTTGAAGT |
| | cDNA | TTGAAGT |
| | Genomic | GTGCCCAAGTACTTCTTGAGGCGGGTGCTGCAGTGGATGCTTTGGACAAG |
| | cDNA | GTGCCCAAGTACTTCTTGAGGCGGGTGCTGCAGTGGATGCTTTGGACAAG |
| | Genomic | AACAAGAACACTCCGCTGCATTACGCCGCTGGCTATGGTATGAAGGGGTG |
| | cDNA | AACAAGAACACTCCGCTGCATTACGCCGCTGGCTATGGTATGAAGGGGTG |
| | Genomic | CGTGGATCTTTTGCTGAAGAACGGAGCCGCTGTGTAAGTTAAACCTGCTC |
| | cDNA | CGTGGATCTTCTGCTGAAGAACGGAGCCGCTGT |
| | Genomic | GCTTTGCTAGTTGCGATCACATCATTTTTTTTGCATTATATTATTTGACT |
| | cDNA | |
| | Genomic | GTCTCGAATTGCATCGCAGCACCCTCGAAAACATGGATGGCAAGACGCCC |
| | cDNA | CACCCTCGAAAACATGGATGGCAAGACGCCC |
| | Genomic | ATTGACGTTGCGA-GCTCAACA-CCAGGAT |
| | cDNA | ATTGACGTTGCGAAGCTCAACAACCAGGATGAGGTTCTCAAGTTGCTGGA |
| | cDNA | AAAGGATGCCTTCCTGTAGATCGCCTTTGTTATTCTCATGGGCGCATGAA |
| | cDNA | CAGTTTGGCTCCAGGATCCGTA |

RANK1 partial cDNA and genomic DNA sequences

FIG. 3A

```
cDNA                TACGGATCCTGCTGCACTGATAAAGTACTGGAAT
Genomic    GACCCAGAAACATTTCGAAAGATCAGCCAGGCAATGGGGCCTTTAGGCGG
cDNA       GACCCAGAAACATTTCGAAAGATCAGCCAGGCAATGGGGCCTTTAGGCGG
Genomic    CCCTGATTTTGCTGAACCTTCTGGAACTGAAGGAACAGAGGAAGAAGGTG
cDNA       CCCTGATTTTGCTGAACCTTCTGGAACTGAAGGAACAGAGGAAGAAGGTG
Genomic    AATATGAAGATGAATCTATCGTCCATCACACTGCCAGTGTCGGTGATGAT
cDNA       AATATGAAGATGAATCTATCGTCCATCACACTGCCAGTGTTGGTGATGAT
Genomic    GAGGTAAGGGGGCAGAGTGCTAAGTAGTACAGCTAAGGATTTGAAATTAT
cDNA       GAGG
Genomic    TACTTCCTCCGTTTCATATTATAACACTTCCTAGCATTGCCCACATTCAT
cDNA
Genomic    ATACATGTTAATGAATCTAGACATATATGTGCGCCTAGATTCATTAATAT
cDNA
Genomic    CTATATGAATATGGGCAATGCTAGAAAGTCTTATAACCTGAAACGGAGGT
cDNA
Genomic    AGTATTGATATTACTATTTAGTCTCGAGCTTGAGAGTTTGTATATGTTTC
cDNA
Genomic    TATGTCTTGTTGGTGTGTAATGTATAATTTACTAGAGAAGTGTCCATTCG
cDNA
Genomic    TGTGTGTGTATGGTTATATAATATCTTCAATTACAGTAATATGCCTCT
cDNA
Genomic    CCGTTTTGGTTTTGCTCTGAACAACATGTATAGGTTTTCGCACAAATTGT
cDNA
Genomic    GATCTCGATGGCCTTTTCTGTTTCATTGTCAATTCAGCTTGCCTTTCTTT
cDNA
Genomic    ACAAGTTTAAGTCATCTAATAGGGTCTGAAGAAAGCTTTAGATGGTGGAG
cDNA                           GTCTGAAGAAGGCTTTAGATGGTGGAG
Genomic    CAGACAAAGACGAACAACACTTGGAGGGCAGAAGGGCCTTACACTTTGTA
cDNA       CAGACAAAGACGAAGAAGACTTGGAGGGCAGAAGGGCCTTACACTTTGTA
Genomic    TGTGGATATGGGGAGGTATGCAAGTCTGCTTAACTAAACCCAATGACAAT
cDNA       TGTGGATACGGGGAG
Genomic    TGAAACCTGTGCAAGTAGAAAATGCCGAATAAATACTACTCCCTCCGTTT
cDNA
Genomic    CATAATGTAAGTCATTCTAGCATTTTTCATATTCATATTGATGTTTATGA
cDNA
Genomic    ATCTAGAAAGACATCAATATGAATGTGGGAAATGCTAGAATGACTTACAT
cDNA
Genomic    TGTGAAACGGAAGAAGTACTATTACCTATTTGTTGTTATTGCAAATGACA
cDNA
Genomic    AGGTTAGCAACTATAAAAACATCTCGTTGCGAATCCTGTGCAAAACGGAT
cDNA
Genomic    TGCATGTATGCGTGACTAGTCTTCAGAAAATTGCATGTATGCAATGTGAC
cDNA
Genomic    AGTTCATTATGCAAAACGGTGAACCTACTGTTGCCATCAGTATCCCCGAT
cDNA
Genomic    ACTAATTGAAGTTCTCCTAATGTTTTCTTTTTTCCTTTTTGGTAATCAGC
cDNA
Genomic    TAGCGTTGAATTCAGCTTAGTTGGGGGCTAACTGTCTTTTTGCATTCTAT
cDNA
Genomic    GATGAGTTTTGACAAATTTATTAATTTTATCTTTTTTTTTTTTTGCTTTT
cDNA
Genomic    AACACACTTCAAGATATTTTTGGTAGATGGAAAGGTGCAGAGCTTGCTGG
cDNA
```
RANK1 partial cDNA and genomic DNA sequences (continued)

FIG. 3B

Full-length cDNA sequence of RANK1.
The predicted amino acid sequence of RANK1 protein is
put under the corresponding coding region.

```
5'GGCCACGCGTCGACTAGTACGGGGGGGGGGGGGGGGCGCTCTCCCTCCACGAGCCAT
CGTCGCTGCACCTCGCGGTCTCCGCCGCTCTCCCTCCACGAGTCGCCGCCGCCGCCAGC
ACTCAGAGAGAGAGAGAGACGGAATACGGGGAGAGACGTAGATATGGATAGGGTTTGGT
CAAGGGTATTTTGGTCATTACGAAAAATAATTGCATTTCTTTCTTTTTAAAAAAATGAA
AACTTAACAGTGTTAAAATCAGGGCCAAACGGAGTGTTCATTTTTAAAAAGTAGGGTCA
AATAAGCAAACTAGAAAAAGTAGGGTCATATTGGTAATTAAGCTTCAAAACAGGGTCAA
ATAAGCAATTACCCCTAAAAAAAAAAGAACTTGTCAGGGCAGATCATACCATCATCACC
CACAGCTCCTTGTAAAGGAGTAAAGAAACTGAAATTGGAAGTTTATCATATCATGTTAG
TTTTTTTTGGTTCATATCCTCATCCTGATAAGAAAAATATCAACCTTGATTGGTGTTA
TAGTAGTAGTTTCTTATGACCGACATTATTTTTGTATTTTAGAATTTGTTTATGTGATT
GTCAGCTGATGAGCTGATAAAATCGAATTGGGAATTATTTGGTGCGTTGGTCAAATCCA
TCTTCATTCATAGTAGTTGCGTTCTAATCCACTTTGCAACCTCAATTTTTCGCGGAAAA
GATTTATAGCATTGCAGCTTCCCTCATATATTGTAAGAAGAAAAGGTAGAAAAGAAGCA
AGGAATCAGTTCTTTTATTCAGCTTCTTTACTAGCCAGTTTT
```

| | | | | | | | | | | | |
|---|---|---|---|---|---|---|---|---|---|---|---|
| ATG | CTT | TGT | TGT | CAA | AGC | TGG | CTA | CGG | TAC | CAT | GCG | ATG | CAT | GTT |
| Met | leu | cys | cys | gln | ser | trp | leu | arg | tyr | his | ala | met | his | val |

| TCT | GAT | TTG | ATC | AAT | TCT | CTT | GCA | GAT | GAG | AAA | AAA | AGT | TCA | AAA |
|---|---|---|---|---|---|---|---|---|---|---|---|---|---|---|
| ser | asp | leu | ile | asn | ser | leu | ala | asp | glu | lys | lys | ser | ser | lys |

| CCA | CAA | GGA | TCA | TCC | AAT | GAT | CAT | CAA | GGG | TTT | CTG | CCA | GGA | GGC |
|---|---|---|---|---|---|---|---|---|---|---|---|---|---|---|
| pro | gln | gly | ser | ser | asn | asp | his | gln | gly | phe | leu | pro | gly | gly |

| TCT | CCT | GCA | AAT | ACT | TTT | GAT | TTT | GCT | TCT | TTG | CAC | AGC | TTG | CTC |
|---|---|---|---|---|---|---|---|---|---|---|---|---|---|---|
| ser | pro | ala | asn | thr | phe | asp | phe | ala | ser | leu | his | ser | leu | leu |

FIG. 6A

```
AAT GAT CCA TCT GTA AAG GAG ATA GCA GAT CAG ATT GCA AAG GAC
asn asp pro ser val lys glu ile ala asp gln ile ala lys asp CCT GCG TTC ACC CAG ATA GCG GAG CAG GCA CTG GAA GGC CAA GGA
pro ala phe thr gln ile ala glu gln ala leu glu gly gln gly GAA CAG GGC ATG CCT GCA ATA GAC CCT TAC ATT GAA ACA ATG CAA
glu gln gly met pro ala ile asp pro tyr ile glu thr met gln AAG TTC ATG GAA AGC CCC CAT TTT TTT ACA ATG GCA GAG CGT CTT
lys phe met glu ser pro his phe phe thr met ala glu arg leu GGG GAT GCT CTT GTG AAG GAT CCT GCA ATG TCC AGT CTG CTG GAA
gly asp ala leu val lys asp pro ala met ser ser leu leu glu AAC TTG ACT AGT CCA ATG CAT AAT GCA AAG ATA GAA GAG CGT GTT
asn leu thr ser pro met his asn ala lys ile glu glu arg val TCT CGT ATG AAG GAA GAT CCA GCC GTG AAA TCA ATT ATG GCT GAG
ser arg met lys glu asp pro ala val lys ser ile met ala glu TTA GAG ACT GGT GAT CCT GCT GCA CTG ATA AAG TAC TGG AAT GAC
leu glu thr gly asp pro ala ala leu ile lys tyr trp asn asp CCA GAA ACA TTT CGA AAG ATC AGC CAG GCA ATG GGG CCT TTA GGC
pro glu thr phe arg lys ile ser gln ala met gly pro leu gly GGC CCT GAT TTT GCT GAA CCT TCT GGA ACT GAA GGA ACA GAG GAA
gly pro asp phe ala glu pro ser gly thr glu gly thr glu glu GAA GGT GAA TAT GAA GAT GAA TCT ATC GTC CAT CAC ACT GCC AGT
glu gly glu tyr glu asp glu ser ile val his his thr ala ser GTT GGT GAT GAT GAG GGT CTG AAG AAG GCT TTA GAT GGT GGA GCA
val gly asp asp glu gly leu lys lys ala leu asp gly gly ala GAC AAA GAC GAA GAA GAC TTG GAG GGC AGA AGG GCC TTA CAC TTT
asp lys asp glu glu asp leu glu gly arg arg ala leu his phe GTA TGT GGA TAT GGG GAG TTG AAG TGT GCC CAA GTA CTT CTT GAG
val cyc gly tyr gly glu leu lys cys ala gln val leu leu glu GCG GGT GCT GCA GTG GAT GCT TTG GAC AAG AAC AAG AAC ACT CCG
ala gly ala ala val asp ala leu asp lys asn lys asn thr pro
```

FIG. 6B

```
CTG CAT TAC GCC GCT GGC TAT GGT ATG AAG GGG TGC GTG GAT CTT
leu his tyr ala ala gly tyr gly met lys gly cyc val asp leu CTG CTG AAG AAC GGA GCC GCT GTC ACC CTC GAA AAC ATG GAT GGC
leu leu lys asn gly ala ala val thr leu glu asn met asp gly AAG ACG CCC ATT GAC GTT GCG AAG CTC AAC AAC CAG GAT GAG GTT
lys thr pro ile asp val ala lys leu asn asn gln asp glu val CTC AAG TTG CTG GAA AAG GAT GCC TTC CTG TAG
leu lys leu leu glu lys asp ala phe leu AMB ATCGCCTTTGTTATTCTCATGGGCGCATGAACAGTTTGGCTCCAGGATCATCATTCTTT
AATTTGCGTCGTTTGGTGCCGCCATTCATATTTCTTTGCTACCCAGTGGCAGTTCATAA
GATACGGTGAAGGGGCTGCCACACAACTGCTGTGGTTCACGATGACTTGTGTACCCCAG
CTTTGTTTCTCTTGTTTTCATTAGTGCAATCGAGATTGTGTATCCACATTTTCTTTTTT
TTTTCAGTATTGCGCATATATGTCTTTTCCTTTTCTGTGAAAAAAAAAAAAAAAAAAAA
AA3'
```

FIG. 6C

RANK1, AN ANKYRIN-REPEAT CONTAINING PEPTIDE FROM RICE ASSOCIATED WITH DISEASE RESISTANCE

This application is a continuation-in-part of PCT international application No. PCT/SG97/00042 which has an international filing date of Sep. 15, 1997, which designated the United States, the entire contents of which are hereby incorporated by reference.

FIELD OF THE INVENTION

Fungal, bacterial and viral diseases in crop plants result in reduced yields and product quality and are responsible for substantial losses to farmers. For example, rice blast, an often devastating disease that occurs in most rice growing areas worldwide, is estimated to cost farmers $5 billion a year (Moffat, 1994). The disease reduces rice yield significantly, particularly in the temperate flooded and tropical upland rice ecosystems. The use of resistant cultivars is the most economical and effective method of controlling the disease. Over the last decades, much has been learned about the genetics of resistance to the blast fungus. Many major genes for resistance have been identified and widely used in breeding programs. However, the molecular mechanism of host resistance to this pathogen is mostly unknown.

When a plant is attacked by a pathogen such as the rice blast fungus, it can in most cases fend off the infection by mounting a battery of defense responses (Lindsay et al., 1993). The activation of plant defense occurs upon pathogen recognition and results in the halt of pathogen ingress. Systemic acquired resistance (SAR) is one important component of this complex system that plants use to defend themselves against pathogens (Ryals et al., 1996). SAR can be triggered by a local hypersensitive response(HR) to an avirulent pathogen, which renders uninfected parts of the plant resistant to a variety of normally virulent pathogens. SAR is a particularly important aspect of plant-pathogen response because it is a pathogen inducible, systemic resistance against a broad spectrum of pathogens.

Significant progress has been made recently in deciphering molecular aspects of SAR. The Arabidopsis gene NPR1/NIM1 has been cloned using a map-based strategy (Cao et al., 1997; Ryals et al., 1997). Mutants with defects in NPRI/NIM1 fail to respond to various SAR-inducing treatments, displaying little expression of pathogenesis-related (PR) genes and exhibiting increased susceptibility to infections. The gene encodes a novel protein containing ankyrin repeats and shows homology to the mammalian signal transduction factor IκB subclass a, suggesting that RPN1/NIM1 may interact with an NF-κB-related transcription factor to induce SAR gene expression and trigger disease resistance (Ryals et al., 1997).

The ankyrin repeat is a 33-amino acid motif present in a number of proteins of diverse functions including transcription factors, cell differentiation molecules, and structural proteins (Bennet, 1993). The ankyrin motif consensus sequence contains the following sequence of amino acids shown as SEQ ID NO:1:

-D----G-TPLH-AA-------V--LL--GA- (LaMarco, 1991). This motif has been shown to mediate protein interactions and is usually present in tandem arrays of four to seven copies (Michaely and Bennett, 1993). Ankyrin repeat-containing proteins have been shown to have diverse functions and to be involved in protein-protein interactions. Some of these proteins in mammals are transcription-regulating proteins, such as the NF-κB, inhibitor IκB (Baldwin, A. 1996; Whiteside et al., 1997). The NF-κB/IκB signal transduction pathways are conserved in both mammals and flies. A stimulus such as IL-1 treatment or bacterial inoculation leads to activation of a signal transduction pathway because of the degradation of IκB or its homolog and the release of the NF-κB transcription factor to the nucleus to stimulate transcription (Baeuerie and Baltimore, 1996; Baldwin, 1996). In Arabidopsis, NPR1/NIM1, which is homologous to the NF-κB inhibitor IκB, controls the onset of SAR. The transcription factor targeted by NPR1/NIM1 serves as a repressor of SAR gene expression and disease resistance either by direct or indirect action (Ryals et al., 1997).

SAR is an important plant defense mechanism against infectious pathogens. For example, evidence suggests that SAR can protect plants against rice blast disease. The SAR inducer benzo (1,2,3)thiadiazole-7-carbothioic acid S-methyl ester ("BHT") was found to be effective in controlling the blast disease in field conditions.

SUMMARY OF THE INVENTION

A gene has been isolated from blast resistant plants that encodes a novel protein containing ankyrin repeats. This gene, designated RANK1, for rice ankyrin repeats, has significant homology to the Arabidopsis gene NPR1/NIM1 and the mammalian signal transduction factor inhibitor I-κB. The RANK1 gene encodes a protein that is believed to play an important role in rice defense to the blast pathogen infection as well as to other diseases which respond through SAR. Since both the RPN1/NIM1 and RANK1 genes code for ankyrin repeats, it is believed that these repeats may be responsible for SAR induced resistance to plant disease, especially rice blast disease.

Accordingly, the present invention provides, in one embodiment thereof, an isolated nucleic acid comprising a sequence of SEQ ID NO:2.

In another embodiment, the invention provides recombinant DNA expression vectors functional in a plant cell comprising a nucleic acid of SEQ ID NO:2.

A third embodiment is a plant cell stably transformed with a nucleic acid comprising a sequence of SEQ ID NO:2.

Yet another embodiment provides a transgenic plant transformed with a nucleic acid comprising a sequence of SEQ ID NO:2.

The invention further provides a method of conferring resistance to disease in a monocotyledonous plant comprising stably integrating into the genome of said plant the nucleic acid having the sequence which codes for a protein comprising the ankyrin motif sequence.

Another embodiment of the invention provides a method of conferring resistance to rice blast disease in a monocotyledonous plant comprising stably integrating into the genome of said plant the nucleic acid having the sequence which codes for a protein comprising the ankyrin motif sequence.

BRIEF DESCRIPTION OF THE DRAWINGS

FIG. 1 Shows the alignment of RANK1's predicted amino acid sequence (SEQ ID NO:3) with Ikβ-E (SEQ ID NO:4), Ikβ-α (SEQ ID NO:5), Cactus (SEQ ID NO:6) and NPR1 (SEQ ID NO:7) proteins containing ankyrin repeats.

FIG. 3 Shows alignment of the RANK1 partial cDNA (SEQ ID NO:2) and genomic DNA (SEQ ID NO:8).

FIG. 6 Shows the full-length cDNA of RANK1 gene (SEQ ID NO:9) which obtained from rice line C101A51 by 5' RACE (5' Rapid Amplification of cDNA Ends), RT-PCR (Reverse Transcriptase-Polymerase Chain Reaction) and screening of a cDNA library. The full-length cDNA of RANK1 is 2127 bp of which the nucleotides from 1 to 999 were obtained by 5' RACE and the nucleotides from 798 to 2127 were inferred from a cDNA clone. The 5' RACE product and the cDNA clone have an overlapping region of 202 bp corresponding to nucleotide position from 798 to 999. The ORF (Open Reading Frame) to RANK1 corresponds to nucleotide position from 808 to 1830 (including the stop code "TAG") which encodes a protein of 340 amino acids.

Figure 2:
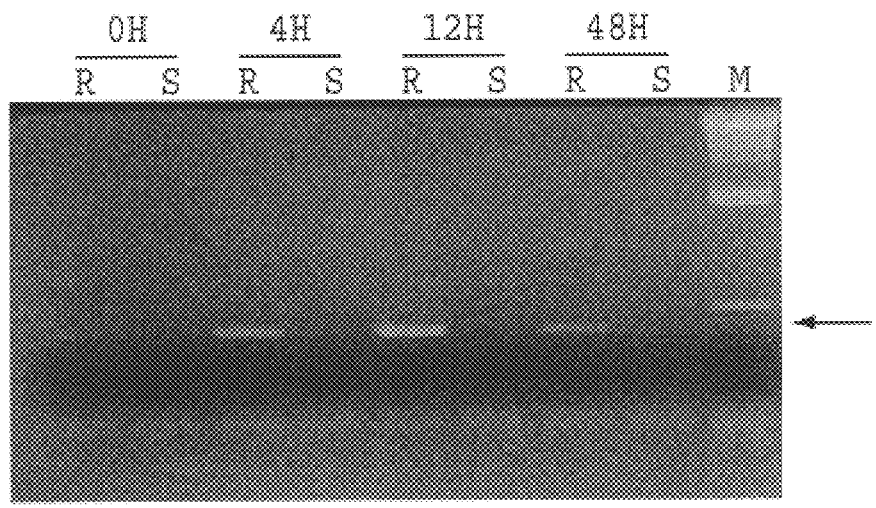
FIG. 2 Agarose gel electrophoresis showing accumulation of NPR1 RNA in blast resistant plants post-inoculation. RANK1 specific primers were used to amplify cDNAs isolated from the resistant (C101A51) and susceptible (CO39) plants.

The partial cDNA (SEQ ID NO:2), is a total of 573 bp which corresponds to nucleotide position from 1311 to 1883 on the full-length cDNA of RANK1 gene.

DETAILED DESCRIPTION OF THE INVENTION

The present invention relates to an isolated nucleic acid conferring resistance to rice blast disease. The nucleic acid codes for a protein which is predicted to have ankyrin repeats. The nucleic acid advantageously has nucleotide sequence SEQ ID NO:2. It will be recognized, however, that the nucleotide sequence may vary, as permitted by the degeneracy of the genetic code while still encoding the same protein. Expression of the gene in a plant may be enhanced by replacing one or more of the codons shown in SEQ ID NO:2 with codons that are preferred by the plant into which the nucleic acid is inserted.

The nucleic acid can be incorporated in plant or bacterium cells using conventional recombinant DNA technologies. Generally, such techniques involve inserting the nucleic acid into a DNA expression vector. Such vector advantageously contains the necessary elements for the transcription and translation of the inserted protein coding sequences and one or more marker sequences to facilitate selection of transformed cells or plants.

A number of plant-active promoters are known in the art and may be used to effect expression of the nucleic acid sequences disclosed herein. Suitable promoters include, for example, the nos promoter, the small subunit chlorophyll A/B binding polypeptide, the 35S promotor of cauliflower mosaic virus, and promoters isolated from plant genes. The promoter may be isolated from the type of plant to be transformed. The 35S or actin promoters may also be used for isolated cDNA clones. These are also useful to test overexpression of the gene.

Once the nucleic acid of the present invention has been cloned into an expression vector, it is ready to be transformed into a plant cell. The term plant cell includes any cell derived from a plant; this includes undifferentiated tissues such as callus and suspension cultures, as well as plant seeds, pollen or plant embryos. Plant tissues suitable transformation include leaf tissues, root tissues, meristems, protoplasts, hypocotyls cotyledons, scutellum, shoot apex, root, immature embryo, pollen, and anther.

One technique of transforming plants with the nucleic acid conferring disease resistance in accordance with the present invention is by contacting tissue of such plants with an inoculum of a bacteria transformed with a vector comprising a nucleic acid in accordance with the present invention. Generally, this procedure involves inoculating the plant tissue with a suspension of bacteria and incubating the tissue for 48 to 72 hours on regeneration medium without antibiotics at 25–28 C.

Bacteria from the genus Agrobacterium can be utilized to transform plant cells. Suitable species of such bacterium include *Agrobacterium tumefaciens* and *Agrobacterium rhizogenes*. *Agrobacterium tumefaciens* (e.g., strains LBA4404 or EHA105) is particularly useful due to its well-known ability to transform plants.

Another approach to transforming plant cells with the nucleic acid of this invention involves propelling inert or biologically active particles at plant cells. This technique is disclosed in U.S. Pat. Nos. 4,945,050, 5,036,006 and 5,100, 792 all to Sanford et. al., which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the nucleic acid conferring disease resistance. Biologically active particles (e.g., dried yeast cells, dried bacterum or a bacteriophage, each containing DNA sought to be introduced) can also be propelled into a plant cell tissue.

Another method of transforming plant cells is the electroporation method. This method involves mixing the protoplasts and the desired nucleic acid and forming holes in the cell membranes by electric pulse so as to introduce the DNA in the cells, thereby transforming the cells. This method currently has high reproducibility and various genes have been introduced into monocotyledons, especially rice plants by this method (Toriyama et. al.,(1988); Shimamoto et al., (1989), Rhodes et al., (1988)).

Similar to the electroporation method is a method in which the desired gene and protoplasts are mixed and the mixture is treated with PEG, thereby introducing the gene into the protoplasts. This method is different from the electroporation method in that polyethylene glycol ("PEG") is used instead of the electric pulse. (Zhang W. et. al., (1988); Datta et al. (1990), Christou et al. (1991)).

Other methods include 1) culturing seeds or embryos with nucleic acids (Topfer R. et al., (1989); Ledoux et al., (1974)); 2) treatment of pollen tube, (Luo et al. (1988)); 3) liposome method (Caboche (1990)); Gad et al. (1990); and 4) the microinjection method (Neuhaus et al. (1987).

Known methods for regenerating plants from transformed plant cells may be used in preparing transgenic plants of the present invention. Generally, explants, callus tissues or suspension cultures can be exposed to the appropriate chemical environment (e.g., cytokinin and auxin) so the newly grown cells can differentiate and give rise to embryos which then regenerate into roots and shoots.

The nucleic acid sequence of the present invention can be used to confer to monocotyledonous plants, resistance to rice blast disease and other diseases regulated by SAR. Such plants include but are not limited to rice, wheat, barley, maize and asparagus.

The invention is further illustrated by the following examples, which are intended to be illustrative and not to be limiting.

EXAMPLES

Materials and Methods

Rice Plants and Blast Inoculation

The resistant isogenic line ClO1A51 carrying the Pi-2 gene and the susceptible cultivar CO39 were used in the experiment. Three-week old rice plants were inoculated with isolate PO6-6 and kept in a dew chamber for 24 hours at 26 C. Leaf tissue was harvested from both cultivars at 0, 4, 8, 12, 24, 48, 72 hours after inoculation.

RNA Isolation and RT-PCR

RNeasy mini kit (Qiagen, USA) was used to isolate total RNA from 150–200 mg rice leaf tissue. Poly(A)+ RNA fractionated from total RNA using Qiagen Oligotex Spin Column, was used as a template in a reverse transcriptase-mediated polymerase chain reaction (RT-PCR) using 10-mer random primers (Operon Technology, Inc). RT-PCR was conducted following protocols provided by the manufacturer (GIBCO-BRL, USA). The amplified cDNAs were then separated in 4.5% sequencing gel.

Cloning and DNA Sequencing

Specific bands were cloned into pGEM-T vector (Promega, USA) Clones were sequenced using the ABI PRISM 377 DNA sequencer (Perkin-Elmer, CA, USA). The sequence was analyzed with softwares DNAstar and Sequencer 3.0.

Results

RANK1 was strongly induced in the resistant plants

Twenty-eight random primers have been used to amplify cDNAs from C1O1A51 and CO39. When primer OPF-1 (ACGGATCCTG; SEQ ID NO:10) was used in the RT-PCR reaction, a specific band (about 600 bp) was observed only in the inoculated resistant plants. It was strongly induced as early as 4 hours post-inoculation. This band was cut from the sequencing gel, re-amplified using the same primer and cloned into the pGEM-T vector. The DNA sequence of this cDNA clone is provided in SEQ ID NO:2. It was compared to databases of known genes to search for homology to known genes. The search revealed that the predicted amino acid sequence of the protein encoded by this gene (RANK1) has significant homology to those proteins containing ankyrin repeats including the Arabidopsis gene RPN1/NIM1 and mammalian gene family IκB (FIG. 1).

A pair of RANK1 specific primers was designed and used to amplify cDNAs isolated from the second inoculation experiment. Amplified cDNAs were run on agarose gel. The 600 bp fragment was only observed in the resistant plants (FIG. 2).

Figure 4:
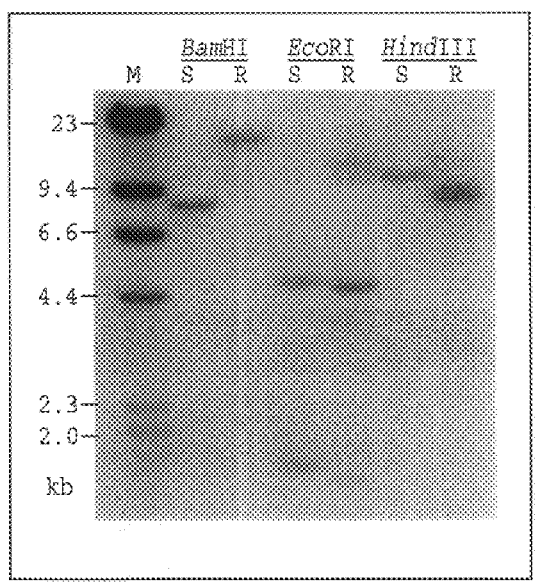
FIG. 4 Shows the Southern analysis of the resistant (C101A51) and susceptible (Co39) plants with the RANK1 gene.
Figure 5:
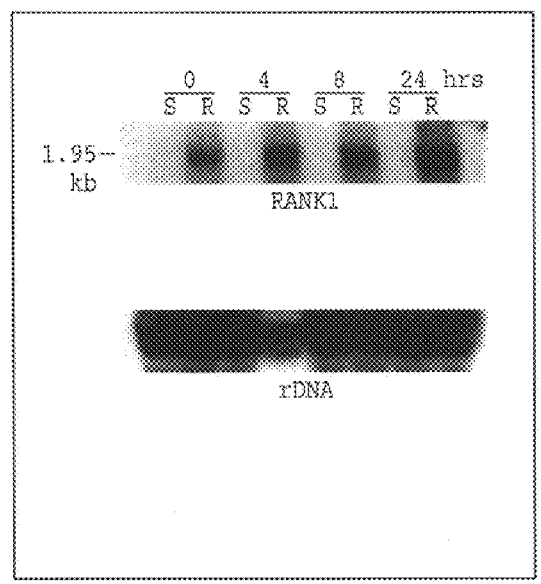
FIG. 5 Shows the Northern analysis of the resistant (C101A51) and susceptible (Co39) plants with the RANK1 gene.

A Southern and Northern Analysis of the resistant (C101A5) and susceptible (CO39) plants were performed as shown in FIGS. 4 and 5.

Isolation of the RANK1 genomic clone from a bacterial artificial chromosome (BAC) library.

The RANKI partial cDNA clone was used as the probe to screen a BAC library made from an indica cultivar IR64. Six positive BAC clones were identified and minipreped for further subcloning. The sequence of a 2.0 kb subclone revealed the presence of introns in the region spanned by the 600 bp cDNA fragment, designating the RANK1 gene. The sequence of the RANK1 genomic clone is set forth in SEQ ID No.:8.

Bibliography

Baeuerie (1996) *Cell* 87:13–20.
Baldwin (1996) *Annu. Rev. Immunol.* 14:649–681.
Bennet (1993) *J. Biol. Chem.* 22703–22709.
Caboche et al. (1990) *Physiol. Plant.* 79:173–176.
Cao et al. (1997) *Cell* 88:57–63.
Christou et al. (1991) *Bio/Technology* 9:957–962.
Datta et al. (1990) *Bio/Technology* 8:736–740.
Gad et al. (1990) *Physiologia Plantarium* 79:177–183.
Gorlach et al. (1996) *The Plant Cell* 8:629–643.
LaMarco et al. (1991) *Science* 253:789–792.
Luo et al. (1988) *Plant Molecular Biology Reporter* 6(3) :165–174.
Maniatis et al. *Molecular Cloning: A Laboratory Manual* (1982).
Moffat (1994) *Science* 265:1804–1805.
Neuhaus et al. (1987) *Theoretical and Applied Genetics* 75:30–36.
Rhodes et al. (1988) *Science* 240:204–207.
Ryals et al. (1997) *The Plant Cell* 9: 425–439.
Shimamoto et al. (1989) *Nature* 338:274–277.
Topfer et al. (1989) *The Plant Cell* 1:133–139.
Toriyama et. al.,(1988) *Bio/Technol.* 6:1072–1074.
Whiteside et al. (1997) *The EMBO Journal* 16:1413–1426.
Zhang et al. (1988) *Theoretical and Applied Genetics* 76:835–840.

What is claimed is:

1. An isolated nucleic acid comprising the sequence of SEQ ID NO:2.

2. An isolated nucleic acid comprising a sequence which codes for the protein encoded by the nucleotide sequence of SEQ ID NO:2.

3. The isolated nucleic acid of claim 1, operatively linked to a promoter active in a plant.

4. The isolated nucleic acid of claim 3, wherein the plant is a monocotyledonous plant.

5. The isolated nucleic acid of claim 3, wherein the plant is selected from the group consisting of rice, barley, corn, wheat, and asparagus.

6. A recombinant DNA expression vector functional in a plant cell comprising the nucleic acid of claim 1.

7. The recombinant DNA expression vector of claim 6 wherein said plant is a monocotyledonous plant.

8. The recombinant DNA expression vector of claim 6 wherein said plant is selected from the group consisting of rice, barley, corn, wheat, and asparagus.

9. A method of making a transgenic monocotyledonous plant, said method comprising:

stably integrating into the genome of a monocotyledonous plant, a nucleic acid comprising the nucleotide sequence of SEQ ID NO:2 wherein said nucleic acid is expressed in said plant.

10. The method according to claim 9, wherein said monocotyledonous plant is a plant selected from the group consisting of rice, barley, corn, wheat and asparagus.

11. A plant cell stably transformed with a nucleic acid comprising the nucleic acid sequence of SEQ ID NO:2.

12. A transgenic plant comprising:

a nucleic acid stably integrated into the plant genome comprising the nucleotide sequence of SEQ ID NO:2; and a plant promoter operatively linked to the nucleic acid such that the sequence is expressed.

13. The transgenic plant according to claim 12 wherein said plant is a monocotyledonous plant.

14. The transgenic plant according to claim 13 wherein said monocotyledonous plant is selected from the group consisting of rice, barley, corn, wheat, and asparagus.

15. An isolated nucleic acid comprising the sequence of SEQ ID NO: 8.

* * * * *

SEQUENCE LISTING

```
<160> NUMBER OF SEQ ID NOS: 10

<210> SEQ ID NO 1
<211> LENGTH: 32
<212> TYPE: PRT
<213> ORGANISM: Arabidopsis sp.
<220> FEATURE:
<221> NAME/KEY: misc_feature
<222> LOCATION: (1)..(1)
<223> OTHER INFORMATION: Xaa = any amino acid
<221> NAME/KEY: misc_feature
<222> LOCATION: (3)..(6)
<223> OTHER INFORMATION: Xaa = any amino acid
<221> NAME/KEY: misc_feature
<222> LOCATION: (8)..(8)
<223> OTHER INFORMATION: Xaa = any amino acid
<221> NAME/KEY: misc_feature
<222> LOCATION: (13)..(13)
<223> OTHER INFORMATION: Xaa = any amino acid
<221> NAME/KEY: misc_feature
```

```
<222> LOCATION: (16)..(22)
<223> OTHER INFORMATION: Xaa = any amino acid
<221> NAME/KEY: misc_feature
<222> LOCATION: (24)..(25)
<223> OTHER INFORMATION: Xaa = any amino acid
<221> NAME/KEY: misc_feature
<222> LOCATION: (28)..(29)
<223> OTHER INFORMATION: Xaa = any amino acid
<221> NAME/KEY: misc_feature
<222> LOCATION: (32)..(32)
<223> OTHER INFORMATION: Xaa = any amino acid
<221> NAME/KEY: misc_feature
<222> LOCATION: (1)..(32)
<223> OTHER INFORMATION: ankyrin motif

<400> SEQUENCE: 1

Xaa Asp Xaa Xaa Xaa Xaa Gly Xaa Thr Pro Leu His Xaa Ala Ala Xaa
1               5                   10                  15

Xaa Xaa Xaa Xaa Xaa Xaa Val Xaa Xaa Leu Leu Xaa Xaa Gly Ala Xaa
            20                  25                  30

<210> SEQ ID NO 2
<211> LENGTH: 573
<212> TYPE: DNA
<213> ORGANISM: Artificial Sequence
<220> FEATURE:
<221> NAME/KEY: misc_feature
<222> LOCATION: (1)..(573)
<223> OTHER INFORMATION: Oryza sp. RANK1 cDNA

<400> SEQUENCE: 2
tacggatcct gctgcactga taaagtactg gaatgaccca gaaacatttc gaaagatcag    60
ccaggcaatg gggcctttag gcggccctga ttttgctgaa ccttctggaa ctgaaggaac   120
agaggaagaa ggtgaatatg aagatgaatc tatcgtccat cacactgcca gtgttggtga   180
tgatgagggt ctgaagaagg ctttagatgg tggagcagac aaagacgaag aagacttgga   240
gggcagaagg gccttacact tgtatgtgg atacgggag ttgaagtgtg cccaagtact    300
tcttgaggcg ggtgctgcag tggatgcttt ggacaagaac aagaacactc cgctgcatta   360
cgccgctggc tatggtatga aggggtgcgt ggatcttctg ctgaagaacg gagccgctgt   420
caccctcgaa acatggatg caagacgcc cattgacgtt gcgaagctca acaaccagga    480
tgaggttctc aagttgctgg aaaaggatgc cttcctgtag atcgcctttg ttattctcat   540
gggcgcatga acagtttggc tccaggatcc gta                                573

<210> SEQ ID NO 3
<211> LENGTH: 172
<212> TYPE: PRT
<213> ORGANISM: Oryza sp.
<220> FEATURE:
<221> NAME/KEY: misc_feature
<222> LOCATION: (1)..(172)
<223> OTHER INFORMATION: RANK1 predicted amino acid sequence

<400> SEQUENCE: 3

Thr Asp Pro Ala Ala Leu Ile Lys Tyr Trp Asn Asp Pro Glu Thr Phe
1               5                   10                  15

Arg Lys Ile Ser Gln Ala Met Gly Pro Leu Gly Gly Pro Asp Phe Ala
            20                  25                  30

Glu Pro Ser Gly Thr Glu Gly Thr Glu Glu Gly Glu Tyr Glu Asp
        35                  40                  45

Glu Ser Ile Val His His Thr Ala Ser Val Gly Asp Asp Glu Gly Leu
    50                  55                  60
```

```
Lys Lys Ala Leu Asp Gly Gly Ala Asp Lys Asp Glu Glu Asp Leu Glu
 65              70                  75                  80

Gly Arg Arg Ala Leu His Phe Val Cys Gly Tyr Gly Glu Leu Lys Cys
                 85                  90                  95

Ala Gln Val Leu Leu Glu Ala Gly Ala Ala Val Asp Ala Leu Asp Lys
            100                 105                 110

Asn Lys Asn Thr Pro Leu His Tyr Ala Ala Gly Tyr Gly Met Lys Gly
            115                 120                 125

Cys Val Asp Leu Leu Lys Asn Gly Ala Ala Val Thr Leu Glu Asn
130                 135                 140

Met Asp Gly Lys Thr Pro Ile Asp Val Ala Lys Leu Asn Asn Gln Asp
145                 150                 155                 160

Glu Val Leu Lys Leu Leu Glu Lys Asp Ala Phe Leu
                165                 170
```

<210> SEQ ID NO 4
<211> LENGTH: 198
<212> TYPE: PRT
<213> ORGANISM: mammalian
<220> FEATURE:
<221> NAME/KEY: misc_feature
<222> LOCATION: (1)..(198)
<223> OTHER INFORMATION: Ik beta-E

<400> SEQUENCE: 4

```
Asp Gly Asp Thr Leu Val His Leu Ala Val Ile His Glu Ala Pro Ala
 1               5                  10                  15

Val Leu Leu Cys Cys Leu Ala Leu Leu Pro Gln Glu Val Leu Asp Ile
                 20                  25                  30

Gln Leu Tyr Gln Thr Ala Leu His Leu Ala Val His Leu Asp Gln Pro
             35                  40                  45

Gly Ala Val Arg Ala Leu Val Leu Lys Gly Ala Ser Arg Ala Leu Gln
         50                  55                  60

Asp Arg His Gly Asp Thr Ala Leu His Val Ala Cys Gln Arg Gln Ser
 65                  70                  75                  80

Trp Pro Val Pro Ala Ala Cys Trp Lys Gly Pro Glu Pro Gly Arg
                 85                  90                  95

Gly Thr Ser Gln Gly Leu Ala Cys Leu His Ile Ala Thr Leu Gln Lys
             100                 105                 110

Asn Gln Pro Leu Met Glu Leu Leu Arg Asn Gly Ala Asp Ile Asp
             115                 120                 125

Val Gln Glu Gly Ser Gly Lys Thr Ala Leu His Leu Ala Val Glu Thr
130                 135                 140

Gln Glu Arg Gly Leu Val Gln Phe Leu Leu Gln Ala Gly Ala Gln Val
145                 150                 155                 160

Asp Ala Arg Met Leu Asn Gly Cys Thr Pro Leu His Leu Ala Ala Gly
                 165                 170                 175

Arg Gly Leu Met Gly Ile Ser Ser Thr Leu Cys Lys Ala Gly Ala Asp
                 180                 185                 190

Ser Leu Leu Arg Asn Val
            195
```

<210> SEQ ID NO 5
<211> LENGTH: 165
<212> TYPE: PRT
<213> ORGANISM: mammalian
<220> FEATURE:
<221> NAME/KEY: misc_feature

```
<222> LOCATION: (1)..(165)
<223> OTHER INFORMATION: Ik beta-a

<400> SEQUENCE: 5

Asp Gly Asp Ser Phe Leu His Leu Ala Ile Ile His Glu Glu Lys Ala
1               5                   10                  15

Leu Thr Met Glu Val Ile Arg Gln Val Lys Gly Asp Leu Ala Phe Leu
            20                  25                  30

Asn Leu Gln Gln Thr Pro Leu His Leu Ala Val Ile Thr Asn Gln Pro
        35                  40                  45

Glu Ile Ala Glu Ala Leu Leu Gly Ala Gly Cys Asp Pro Glu Leu Arg
    50                  55                  60

Asp Phe Arg Gly Asn Thr Pro Leu His Leu Ala Cys Phe Gln Gly Cys
65                  70                  75                  80

Leu Ala Ser Val Gly Val Leu Thr Gln Ser Cys Thr Thr Pro His Leu
                85                  90                  95

His Ser Ile Asn Gly His Thr Cys Leu His Leu Ala Ser Ile His Gly
            100                 105                 110

Tyr Leu Gly Ile Val Glu Leu Leu Val Ser Leu Gly Ala Asp Val Asn
        115                 120                 125

Ala Gln Glu Pro Asn Gly Arg Thr Ala Leu His Leu Ala Val Asp Leu
    130                 135                 140

Gln Asn Pro Asp Leu Val Ser Leu Leu Leu Lys Cys Gly Ala Asp Val
145                 150                 155                 160

Asn Arg Val Thr Tyr
                165

<210> SEQ ID NO 6
<211> LENGTH: 198
<212> TYPE: PRT
<213> ORGANISM: Cactus

<400> SEQUENCE: 6

Asp Gly Asp Thr Pro Leu His Leu Ala Cys Ile Ser Gly Ser Val Asp
1               5                   10                  15

Val Val Ala Ala Leu Ile Arg Met Ala Pro His Pro Cys Leu Leu Asn
            20                  25                  30

Ile Val Ala Gln Thr Pro Leu His Leu Ala Ala Leu Thr Ala Gln Pro
        35                  40                  45

Asn Ile Met Arg Ile Leu Leu Leu Ala Gly Ala Glu Pro Thr Val Arg
    50                  55                  60

Asp Arg His Gly Asn Thr Ala Leu His Leu Ser Cys Ile Ala Gly Glu
65                  70                  75                  80

Lys Gln Cys Val Arg Ala Leu Thr Glu Lys Phe Gly Ala Thr Glu Ile
                85                  90                  95

His Glu Ala Asp Gly Glu Arg Cys Val His Leu Ala Ala Glu Ala Gly
            100                 105                 110

His Ile Asp Ile Leu Arg Leu Leu Val Ser His Gly Ala Asp Ile Asn
        115                 120                 125

Ala Arg Glu Gly Ser Gly Arg Thr Pro Leu His Ile Ala Ile Glu Gly
    130                 135                 140

Cys Asn Glu Asp Leu Ala Asn Phe Leu Leu Asp Glu Cys Glu Lys Leu
145                 150                 155                 160

Asn Leu Glu Thr Ala Ala Gly Leu Thr Ala Tyr Gln Phe Ala Cys Ile
                165                 170                 175
```

```
Met Asn Lys Ser Arg Met Gln Asn Ile Leu Glu Lys Arg Gly Ala Glu
            180                 185                 190

Thr Val Thr Pro Pro Asp
        195

<210> SEQ ID NO 7
<211> LENGTH: 165
<212> TYPE: PRT
<213> ORGANISM: Arabidopsis sp.
<220> FEATURE:
<221> NAME/KEY: misc_feature
<222> LOCATION: (1)..(165)
<223> OTHER INFORMATION: NPR1 protein

<400> SEQUENCE: 7

Ala Ala Val Lys Leu Glu Leu Lys Glu Ile Ala Lys Asp Tyr Glu Val
1               5                   10                  15

Gly Phe Asp Ser Val Val Thr Val Leu Ala Tyr Val Tyr Ser Ser Arg
            20                  25                  30

Val Ile Pro Glu Leu Ile Thr Leu Tyr Gln Arg His Leu Leu Asp Val
        35                  40                  45

Val Asp Lys Val Val Ile Glu Asp Thr Leu Val Ile Leu Lys Leu Ala
    50                  55                  60

Asn Ile Ile Val Lys Ser Asn Val Asp Met Val Ser Leu Glu Lys Ser
65                  70                  75                  80

Leu Pro Glu Glu Leu Val Lys Glu Ile Ile Asp Arg Arg Lys Glu Leu
                85                  90                  95

Gly Leu Glu Asp Ala Cys Ala Leu His Phe Ala Val Ala Tyr Cys Asn
            100                 105                 110

Val Lys Thr Ala Thr Asp Leu Leu Lys Leu Asp Leu Ala Asp Val Asn
        115                 120                 125

His Arg Asn Pro Arg Gly Tyr Thr Val Leu His Val Ala Ala Met Arg
    130                 135                 140

Lys Glu Pro Gln Leu Ile Leu Ser Leu Leu Glu Lys Gly Ala Ser Ala
145                 150                 155                 160

Ser Glu Ala Thr Leu
                165

<210> SEQ ID NO 8
<211> LENGTH: 1978
<212> TYPE: DNA
<213> ORGANISM: Oryza sp.

<400> SEQUENCE: 8
gacccagaaa catttcgaaa gatcagccag gcaatggggc ctttaggcgg ccctgatttt    60
gctgaacctt ctggaactga aggaacagag gaagaaggtg aatatgaaga tgaatctatc   120
gtccatcaca ctgccagtgt cggtgatgat gaggtaaggg ggcagagtgc taagtagtac   180
agctaaggat ttgaaattat tacttcctcc gtttcatatt ataacacttc ctagcattgc   240
ccacattcat atacatgtta atgaatctag acatatatgt cgcctagat tcattaatat    300 ctatatgaat atgggcaatg ctagaaagtc ttataacctg aaacggaggt agtattgata   360
ttactattta gtctcgagct tgagagtttg tatatgtttc tatgtcttgt tggtgtgtaa   420
tgtataattt actagagaag tgtccattcg tgtgtgtgtg tatggttata taatatcttc   480
aattacagta atatgcctct ccgttttggt tttgctctga acaacatgta taggttttcg   540
cacaaattgt gatctcgatg gcctttctg tttcattgtc aattcagctt gccttctt     600
```

-continued

| | |
|---|---|
| acaagtttaa gtcatctaat agggtctgaa gaaagcttta gatggtggag cagacaaaga | 660 |
| cgaacaacac ttggagggca gaagggcctt acactttgta tgtggatatg gggaggtatg | 720 |
| caagtctgct taactaaacc caatgacaat tgaaacctgt gcaagtagaa atgccgaat | 780 |
| aaatactact ccctccgttt cataatgtaa gtcattctag cattttcat attcatattg | 840 |
| atgtttatga atctagaaag acatcaatat gaatgtggga aatgctagaa tgacttacat | 900 |
| tgtgaaacgg aagaagtact attacctatt tgttgttatt gcaaatgaca aggttagcaa | 960 |
| ctataaaaac atctcgttgc gaatcctgtg caaaacggat tgcatgtatg cgtgactagt | 1020 |
| cttcagaaaa ttgcatgtat gcaatgtgac agttcattat gcaaacggt gaacctactg | 1080 |
| ttgccatcag tatccccgat actaattgaa gttctcctaa tgttttcttt tttccttttt | 1140 |
| ggtaatcagc tagcgttgaa ttcagcttag ttgggggcta actgtcttt tgcattctat | 1200 |
| gatgagtttt gacaaattta ttaatttat ctttttttt ttttgctttt aacacacttc | 1260 |
| aagatatttt tggtagatgg aaaggtgcag agcttgctgg tttactttgt tgaagctaaa | 1320 |
| actttgttag ttttctggg gcagttcatt gatgataatc cagacctcac aggtcaacca | 1380 |
| acagtcctcg gtttcaaaaa aaaaaaaaa tcccacagta acctgtcccg ttgaacattg | 1440 |
| cacaaacttg tcagatctgg tgcacctctc gtctagctat aatagtatcg aactatgagt | 1500 |
| ttccataacc ccgctgtttg tataattgca gttggtgtgc aatgctagag cacaaaagtt | 1560 |
| aatgaacgac aaactacctt ttgattcatt ctcttgtgga tctagaatgt ggtgtgagac | 1620 |
| ttttttttg ggagctgcat ctgctccttg ttcactgact aatcaggatt tgggttaaac | 1680 |
| ttttgttttt cagttgaagt gtgcccaagt acttcttgag gcgggtgctg cagtggatgc | 1740 |
| tttggacaag aacaagaaca ctccgctgca ttacgccgct ggctatggta tgaaggggtg | 1800 |
| cgtggatctt tgctgaaga acggagccgc tgtgtaagtt aaacctgctc gctttgctag | 1860 |
| ttgcgatcac atcatttttt ttgcattata ttatttgact gtctcgaatt gcatcgcagc | 1920 |
| accctcgaaa acatggatgg caagacgccc attgacgttg cgagctcaac accaggat | 1978 |

<210> SEQ ID NO 9
<211> LENGTH: 2127
<212> TYPE: DNA
<213> ORGANISM: Oryza sp.
<220> FEATURE:
<221> NAME/KEY: misc_feature
<222> LOCATION: (1)..(2127)
<223> OTHER INFORMATION: cDNA

<400> SEQUENCE: 9

| | |
|---|---|
| ggccacgcgt cgactagtac gggggggggg gggggcgct ctccctccac gagccatcgt | 60 |
| cgctgcacct cgcggtctcc gccgctctcc ctccacgagt cgccgccgcc gccagcactc | 120 |
| agagagagag agagacggaa tacggggaga gacgtagata tggatagggt ttggtcaagg | 180 |
| gtattttggt cattacgaaa ataattgca tttctttctt tttaaaaaa tgaaaactta | 240 |
| acagtgttaa atcagggcc aaacggagtg ttcattttta aaagtaggg tcaaataagc | 300 |
| aaactagaaa aagtagggtc atattggtaa ttaagcttca aaacagggtc aaataagcaa | 360 |
| ttaccccctaa aaaaaaaga acttgtcagg gcagatcata ccatcatcac ccacagctcc | 420 |
| ttgtaaagga gtaaagaaac tgaaattgga agtttatcat atcatgttag ttttttttgg | 480 |
| ttcatatcct catcctgata agaaaaatat caacctgat ttggtgttat agtagtagtt | 540 |
| tcttatgacc gacattattt ttgtatttta gaatttgttt atgtgattgt cagctgatga | 600 |
| gctgataaaa tcgaattggg aattatttgg tgcgttggtc aaatccatct tcattcatag | 660 |

```
                                                -continued tagttgcgtt ctaatccact ttgcaacctc aattttcgc ggaaaagatt tatagcattg         720
cagcttccct catatattgt aagaagaaaa ggtagaaaag aagcaaggaa tcagttcttt         780
tattcagctt ctttactagc cagttttatg ctttgttgtc aaagctggct acggtaccat         840
gcgatgcatg tttctgattt gatcaattct cttgcagatg agaaaaaaag ttcaaaacca         900
caaggatcat ccaatgatca tcaagggttt ctgccaggag gctctcctgc aaatactttt         960
gattttgctt ctttgcacag cttgctcaat gatccatctg taaaggagat agcagatcag        1020
attgcaaagg accctgcgtt cacccagata gcggagcagg cactggaagg ccaaggagaa        1080
cagggcatgc ctgcaataga cccttacatt gaaacaatgc aaaagttcat ggaaagcccc        1140
cattttttta caatggcaga gcgtcttggg gatgctcttg tgaaggatcc tgcaatgtcc        1200
agtctgctgg aaaacttgac tagtccaatg cataatgcaa agatagaaga gcgtgtttct        1260
cgtatgaagg aagatccagc cgtgaaatca attatggctg agttagagac tggtgatcct        1320
gctgcactga taaagtactg gaatgaccca gaaacatttc gaaagatcag ccaggcaatg        1380 gggccttag gcggccctga ttttgctgaa ccttctggaa ctgaaggaac agaggaagaa        1440
ggtgaatatg aagatgaatc tatcgtccat cacactgcca gtgttggtga tgatgagggt        1500
ctgaagaagg ctttagatgg tggagcagac aaagacgaag aagacttgga gggcagaagg        1560
gccttacact ttgtatgtgg atatggggag ttgaagtgtg cccaagtact tcttgaggcg        1620
ggtgctgcag tggatgcttt ggacaagaac aagaacactc cgctgcatta cgccgctggc        1680
tatggtatga agggtgcgt ggatcttctg ctgaagaacg gagccgctgt caccctcgaa        1740
aacatggatg gcaagacgcc cattgacgtt gcgaagctca acaaccagga tgaggttctc        1800
aagttgctgg aaaaggatgc cttcctgtag atcgcctttg ttattctcat gggcgcatga        1860
acagtttggc tccaggatca tcattcttta atttgcgtcg tttggtgccg ccattcatat        1920
ttctttgcta cccagtggca gttcataaga tacggtgaag gggctgccac acaactgctg        1980
tggttcacga tgacttgtgt accccagctt tgtttctctt gttttcatta gtgcaatcga        2040
gattgtgtat ccacatttc tttttttttt cagtattgcg catatatgtc ttttcctttt        2100
ctgtgaaaaa aaaaaaaaaa aaaaaaa                                            2127

<210> SEQ ID NO 10
<211> LENGTH: 10
<212> TYPE: DNA
<213> ORGANISM: Artificial Sequence
<220> FEATURE:
<221> NAME/KEY: misc_feature
<222> LOCATION: (1)..(10)
<223> OTHER INFORMATION: OPF-1 primer

<400> SEQUENCE: 10
acggatcctg                                                                10
```